United States Patent
Gregersen et al.

(10) Patent No.: US 11,466,257 B2
(45) Date of Patent: Oct. 11, 2022

(54) CELL-DERIVED VIRAL VACCINES WITH LOW LEVELS OF RESIDUAL CELL DNA

(71) Applicant: Seqirus UK Limited, Berkshire (GB)

(72) Inventors: Jens-Peter Gregersen, Marburg (DE); Holger Kost, Marburg (DE)

(73) Assignee: Seqirus UK Limited, Berkshire (GB)

( * ) Notice: Subject to any disclaimer, the term of this patent is extended or adjusted under 35 U.S.C. 154(b) by 0 days.

(21) Appl. No.: 16/843,940

(22) Filed: Apr. 9, 2020

(65) Prior Publication Data

US 2020/0377864 A1 Dec. 3, 2020

Related U.S. Application Data

(62) Division of application No. 12/092,190, filed as application No. PCT/IB2006/003880 on Nov. 1, 2006, now Pat. No. 10,655,108.

(60) Provisional application No. 60/732,786, filed on Nov. 1, 2005.

(51) Int. Cl.
| | |
|---|---|
| *C12N 7/00* | (2006.01) |
| *A61K 39/145* | (2006.01) |
| *A61K 39/12* | (2006.01) |
| *A61K 39/00* | (2006.01) |

(52) U.S. Cl.
CPC .............. *C12N 7/00* (2013.01); *A61K 39/12* (2013.01); *A61K 39/145* (2013.01); *A61K 2039/5252* (2013.01); *C12N 2760/16134* (2013.01); *C12N 2760/16151* (2013.01); *C12N 2760/16234* (2013.01)

(58) Field of Classification Search
None
See application file for complete search history.

(56) References Cited

U.S. PATENT DOCUMENTS

| | | |
|---|---|---|
| 4,064,232 A | 12/1977 | Bachmayer et al. |
| 5,010,112 A | 4/1991 | Macfarlane |
| 5,010,183 A | 4/1991 | Macfarlane |
| 5,162,112 A | 11/1992 | Oxford et al. |
| 5,824,536 A | 10/1998 | Webster et al. |

(Continued)

FOREIGN PATENT DOCUMENTS

| | | |
|---|---|---|
| EP | 0 870 508 | 10/1998 |
| EP | 1 108 787 | 6/2001 |

(Continued)

OTHER PUBLICATIONS

Olsen et al., "The emergence of novel swine influenza viruses in North America," Virus Research 85: 199-210 (Year: 2002).*

(Continued)

*Primary Examiner* — M Franco G Salvoza
(74) *Attorney, Agent, or Firm* — Finnegan, Henderson, Farabow, Garrett & Dunner, LLP

(57) ABSTRACT

The present invention relates to vaccine products for the treatment or prevention of viral infections. Further provided are methods of reducing contaminants associated with the preparation of cell culture vaccines. Residual functional cell culture DNA is degraded by treatment with a DNA alkylating agent, such as β-propiolactone (BPL), thereby providing a vaccine comprising immunogenic proteins derived from a virus propagated on cell culture, substantially free of residual functional cell culture DNA.

13 Claims, 3 Drawing Sheets

(56) References Cited

U.S. PATENT DOCUMENTS

Figure 1:
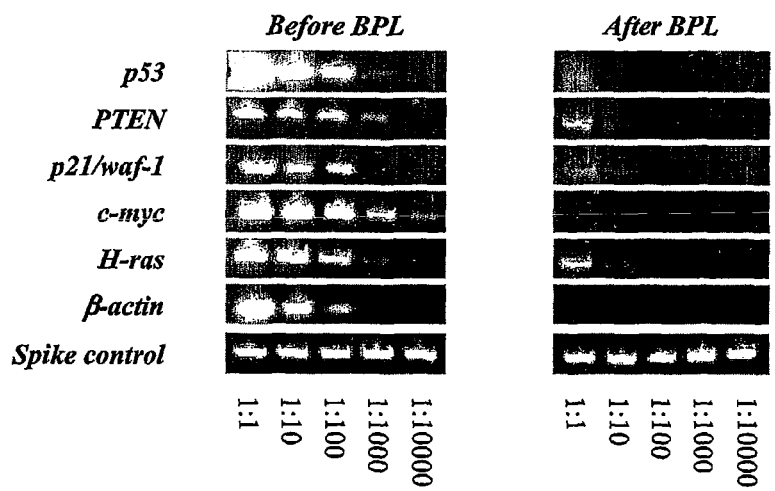

| | | | |
|---|---|---|---|
| 5,948,410 | A | 9/1999 | Van Scharrenburg et al. |
| 6,544,518 | B1 * | 4/2003 | Friede .................... A61P 37/04 424/184.1 |
| 2004/0071734 | A1 | 4/2004 | Garcon et al. |
| 2006/0257852 | A1 | 11/2006 | Rappuoli et al. |

FOREIGN PATENT DOCUMENTS

| | | |
|---|---|---|
| JP | 03-108480 | 5/1991 |
| JP | 2000-230931 | 8/2000 |
| JP | 2005-170945 | 6/2005 |
| WO | WO 1997/37000 | 10/1997 |
| WO | WO 2001/021151 | 3/2001 |
| WO | WO 01/38362 | 5/2001 |
| WO | WO 2002/28422 | 4/2002 |
| WO | WO 02/074336 | 9/2002 |
| WO | WO 2002/067983 | 9/2002 |
| WO | WO 02/087494 | 11/2002 |
| WO | WO 02/097072 | 12/2002 |
| WO | WO 2003/023025 | 3/2003 |
| WO | WO 2003/091401 | 11/2003 |
| WO | WO 2004/112831 | 12/2004 |
| WO | WO 2005/055957 | 6/2005 |
| WO | WO 2006/027698 | 3/2006 |

OTHER PUBLICATIONS

Shu et al., "Genetic reassortment in pandemic and interpandemic influenza viruses," European Journal of Epidemiology, 12:63-70 (Year: 1996).*
Webster et al., "Evolution and Ecology of Influenza Viruses,"vol. 56, No. 1: 152-179 (Year: 1992).*
Jeon et al., "Immunization with Influenza Virus Hemagglutinin Globular Region Containing the Receptor-Binding Pocket," Viral Immunology, vol. 15, No. 1, pp. 165-176, 2002.
Young et al., "Efficient expression of influenza virus NS1 nonstructural proteins in *Escherichia coli*," Proc. Natl. Acad. Sci. USA, vol. 80, pp. 6105-6109, 1983.
English Translation of Notice of Reasons for Rejection, dated Nov. 27, 2017 in corresponding Japanese Patent Application No. 2014-149517, 51 pages.
Office Action dated Dec. 15, 2017 in corresponding Canadian Patent Application No. 2,627,971, 4 pages.
Wickramasinghe et al., "Tangential Flow Microfiltration and Ultrafiltration for Human Influenza A Virus Concentration and Purification," Biotechnology and Bioengineering, 2005, 92(2), pp. 199-208.
GSK's Written Submission in EP 2,301,572, dated Aug. 10, 2017, 11 pages.
Polley et al., "The use of beta-propiolactone for the preparation of virus vaccines. II. Antigenicity," Can J Microbial., 1957, 3(6):871-887.
Bobola et al., "Apurinic endonuclease activity in adult gliomas and time to tumor progression after alkylating agent-based chemotherapy and after radiotherapy," Clin Cancer Res., 2004, 10(23):7875-7883.
Henry, Plant Genotyping II: SNP Technology, CAB International (2008).
Decision to grant a European patent, EP 2301572, dated Aug. 14, 2014, 2 pages.
Decision to maintain EP 1951296, dated Jun. 26, 2014, 1 page.
Interlocutory decision in opposition proceedings, filed in opposition against EP 1951296, dated Oct. 8, 2013, 32 pages.
Minutes of the oral proceedings, filed in opposition against EP 1951296, dated Sep. 12, 2013, 21 pages.
Notice of Appeal by Crucell Holland B.V., dated Dec. 16, 2013, 2 pages.
Notice of Appeal by GlaxoSmithKline Biologicals, dated Dec. 2, 2013, 2 pages.
Termination of opposition proceedings of EP 1951296, dated Jun. 20, 2014, 2 pages.
Third Party Observations by GlaxoSmithKline about EP 2301572, dated Oct. 4, 2013, 6 pages.
Written submission in preparation to oral proceedings by Crucell Holland, filed in opposition against EP 1951296, dated Jul. 12, 2013, 17 pages.
Written submission in preparation to oral proceedings by GlaxoSmithKline Biologicals, filed in opposition against EP 1951296, dated Jul. 12, 2013, 10 pages.
Written submission in preparation to oral proceedings by patentee, filed in opposition against EP 1951296, dated Jun. 14, 2013, 10 pages.
Morgeaux et al., "B-propiolactone treatment impairs the biological activity of residual DNA from BHK-21 cells infected with rabies virus," Vaccine vol. 11(1): 82-90 (1993).
Center for Disease Control (2012), "Influenza," in Epidemiology and Prevention of Vaccine-Preventable Diseases, 12th Edition, pp. 151-172.
Cinkaya et al. (2004), "Abstract #01969 Detail: Novel process for a MOCK suspension cell culture derived influenza subunit vaccine," poster at First International Conference on Influenza Vaccines for the World, Lisbon, Portugal, 2 pages.
Declaration made by Benoit Baras, Oct. 9, 2012, 1 page.
GlaxoSmithKline (2004), "Memorandum—Research & Development," Influenza Vaccines for the World, May 24-26, 2004, 25 pages.
GlaxoSmithKline Biologicals SA (2012), "Data Generated by GlaxoSmithKline Biologicals SA," prepared in opposition to EP 1951296, 4 pages.
GlaxoSmithKline Biologicals SA (Oct. 23, 2012), Response filed in Opposition to European Patent EP 1951296, 5 pages.
Prior Separation Technology (2010), "Memo: Strategies for DNA removal," 2 pages.
Soltec Bio Science, "Purified Detergents: Mega 9," retrieved online in 2011 at: http://www.soltecventures.com/meqa9.htm, 1 page.
Solvay Pharmaceuticals (Nov. 16, 2005), "MOCK as a substitute for influenza vaccine production," presentation to VRBPAC, 41 pages.
Toews et al. (2008), "Mass spectrometric identification of formaldehyde-induced peptide modifications under in vivo protein cross-lining conditions," Analytica Chimica Acta 618:168-183.
Lo Grippo et al. "Investigations of the Use of Beta propiolactone in Virus Inactivation," Annals of the New York Academy of Sciences, vol. 83, pp. 578-594 (1960).
Blackburn et al. (1999), "A study of the effect of chemical inactivants on the epitopes of Rift Valley fever virus glycoproteins using monoclonal antibodies," J Viral Methods 33:367-374.
Budowsky et al. (1993), "Principles of selective inactivation of viral genome. VIII. The influence of β-propiolactone on immunogenic and protective activities of influenza virus," Vaccine 11 :343-348.
Chiron (Nov. 16, 2005), "Use of MDCK cells for manufacture of inactivated influenza virus vaccines," Presentation to VRBPAC, 35 pages.
Chiron Vaccines (Nov. 16, 2005), "Influenza Cell Culture Subunit Vaccine; Vaccines and Related Biological Products Advisory Committee (VRBPAC)," 13 pages.
Cinkaya et al. (2004), "Novel process for a MOCK suspension cell culture derived influenza subunit vaccine," First International Conference on Influenza Vaccines for the World, Lisbon, Portugal, 2 pages.
Dimmock et al. (1986), "Protection of mice from lethal influenza: evidence that defective interfering virus modulates the immune response and not virus multiplication," J Gen Viral 67:839-850.
Fluvax—Summary of Product Characteristics (1998). 6 pages (including English translation of first two sections).
Habib et al. (2006), "Immunogenicity of formaldehyde and binary ethylenimine inactivation infectious bursal disease virus in broiler chicks," J. Zhejiang Univ. Science B. 7:660-664.
Halperin et al. (2002), "Safety and immunogenicity of a trivalent, inactivated, mammalian cell culture-derived influenza vaccine in healthy adults, seniors, and children," Vaccine 20:1240-1247.
Kreil et al. (2005), "Characterization of different strains of poliovirus and influenza virus by differential scanning calorimetry," Biotechnol Appl Biochem., 41 :241-246.

(56) References Cited

OTHER PUBLICATIONS

Merten et al. (1996), "Production of influenza virus in cell culture for vaccine preparation," In: Novel Strategies in Design and Production of Vaccines. Edited by S Cohen and A Shafferman, Plenum Press, New York, pp. 141-151.
Nicholson et al. (1979), "Clinical studies of monovalent inactivated whole virus and subunit A/USSR/77 (H1N1) vaccine: serological responses and clinical reactions," J Biol Standardization 7:123-136.
Notice of Opposition filed by Crucell on Oct. 11, 2011 for EP 1951296, 19 pages.
Notice of Opposition filed by GlaxoSmithKline Biologicals on Oct. 12, 2011 for EP 1951296, 25 pages.
Reichl et al. (Feb. 2000), "ISCOM Vaccines—Antigen production and downstream processing," Proceedings of the 4th International Congress on Biochemical Engineering, Stuttgart, Germany, pp. 314-318.
Sections 869 and 158 in European Pharmacopoeia, Second Edition, part II, Eighteenth Fascicule, (1994), 12 pages.
Stephenson and Nicholson (2001), "Influenza: vaccination and treatment," Eur. Respir. J., 17:1282-1293.
Stevens et al. (Aug. 2010), "Receptor specificity and influenza A H3N2 viruses isolated in mammalian cells and embryonated chicken eggs," J Viral, 84(16):8287-8299.
Tomanee et al. (2004), "Fractionation of protein, RNA, and plamid DNA in centrifugal precipitation chromatography using cationic surfactant CTAB containing inorganic salts NaCl and $NH_4Cl$," Biotechnol Bioenq., 88(1): 52-9.
WHO (1995), "Cell culture as a substrate for the production of influenza vaccines: Memorandum from a WHO meeting," Bulletin of the World Health Organization, 73:431-435.
WHO (Nov. 2003), "Recommendations for production and control of influenza vaccine (inactivated)," 33 pages.
Chappell et al., "Preparation of La Crosse Virus Hemagglutinating Antigen in BHK-21 Suspension Cell Cultures," Applied Microbiology, 1969, vol. 18, No. 3, pp. 433-437.
Frazatti-Gallina et al., "Vero-cell rabies vaccine produced using serum-free medium," Vaccine, 23, 511-17, Dec. 9, 2004.
Kalbfuss et al., "Harvesting and concentration of human influenza A virus produced in serum-free mammalian cell culture for the production of vaccines," Biotechnol. Bioengineering, 97, 73-85, May 1, 2007.
Lalosevic et al., "Immunogenicity of BHK-rabies vaccine in human volunteers," Medicinski Pregled 51, 17-19, 1998.
Morgeaux et al., "Beta-propiolactone treatment impairs the biological activity of residual DNA from BHK-21 cells infected with rabies virus," Vaccine 11, 82-90, 1993.
Perrin et al., "Inactivation of DNA by beta-propiolactone," J. int. Assoc. Biol. Standardization, 23, 207-11, Sep. 1995.
Van Wezel et al., "Detection and elimination of cellular nucleic acids in biologicals produced on continuous cell lines," Developments in Biological Standardization, 50, 59-69, 1981.

\* cited by examiner

CELL-DERIVED VIRAL VACCINES WITH LOW LEVELS OF RESIDUAL CELL DNA

CROSS-REFERENCE TO RELATED APPLICATIONS

This application is a continuation of U.S. patent application Ser. No. 12/092,190, filed Sep. 3, 2008, which is the U.S. National Phase entry under 35 U.S.C. § 371 of International Patent Application No. PCT/IB2006/003880, filed Nov. 1, 2006, which claims benefit of priority to U.S. Provisional Patent Application No. 60/732,786, filed Nov. 1, 2005, all of which are incorporated herein by reference in their entirety.

All documents and on-line information cited herein are incorporated by reference in their entirety.

TECHNICAL FIELD

The invention provides improved cell culture products and processes with reduced impurities. Specifically, the invention provides an improved method of degrading any residual functional cell culture DNA remaining associated with the cell culture generated product. According to the invention, residual functional cell culture DNA is degraded by treatment with a DNA alkylating agent, such as β-propiolactone (BPL). This process may be used to treat a range of cell culture products including vaccines and recombinant proteins.

BACKGROUND ART

Commercial production of viral vaccines typically require large quantities of virus as an antigen source. Commercial quantities of virus for vaccine production may be achieved by culture and replication of a seed virus in a cell culture system. Cell culture systems suitable for viral replication include mammalian, avian or insect cells, but mammalian cell culture systems are particularly preferred for viral vaccines to ensure proper glycosylation and folding of the virus' antigens proteins. For similar reasons, mammalian cell culture systems are also preferred for recombinant protein expression.

If unmodified from their naturally occurring states, cell cultures have a limited ability to reproduce, and subsequently are impractical and inefficient for producing the amount of material necessary for a commercial vaccine or recombinant protein. Consequently, for manufacturing purposes, it is preferred that the cells are modified to be "continuous" or "immortalized" cell lines to increase the number of times they can divide. Many of these modifications employ mechanisms similar to those which are implicated in oncogenic cells. As such, there is a concern that any residual materials from the cell culture process, such as host cell DNA, be removed from the final formulation of a vaccine or recombinant protein product manufactured in these systems.

A standard way of removing residual host cell DNA is by DNase treatment. A convenient method of this type is disclosed in European patent 0870508 and U.S. Pat. No. 5,948,410, involving a two-step treatment, first using a DNase (e.g. Benzonase) and then a cationic detergent (e.g. CTAB).

Current efforts to reduce this risk have focused on reducing the total concentration of residual host cell DNA. It is an object of the present invention to reduce the risk further by eliminating the functionality of any remaining host cell DNA.

SUMMARY OF THE INVENTION

The invention provides improved cell culture products and processes with reduced impurities. Specifically, the invention provides an improved method of degrading any residual functional cell culture DNA remaining associated with the cell culture generated product. According to the invention, residual functional cell culture DNA is degraded by treatment with a DNA alkylating agent, such as β-propiolactone (BPL). This process may be used to treat a range of cell culture products including vaccines and recombinant proteins.

The invention includes a vaccine comprising immunogenic proteins derived from a virus propagated on cell culture, wherein the vaccine is substantially free of residual functional cell culture DNA. In addition, the invention relates to recombinant proteins expressed in cell culture, where the final recombinant protein formulation is substantially free of residual functional cell culture DNA.

Functionality of any residual host cell DNA may be eliminated by treatment of the DNA with an alkylating agent which cleaves the DNA into portions small enough so that it is unable to code for a functional protein, to be transposed into a human recipient's chromosome, or otherwise recognized by recipient DNA replication machinery. Preferably, the length of degraded residual cell culture DNA is less than 500 base pairs. More preferably, the length of degraded residual cell culture DNA is less than 200 base pairs.

DETAILED DESCRIPTION

The invention provides improved cell culture products and processes with reduced impurities. Specifically, the invention provides an improved method of degrading any residual functional cell culture DNA remaining associated with the cell culture generated product. According to the invention, residual functional cell culture DNA is degraded by treatment with a DNA alkylating agent, such as β-propiolactone (BPL). This process may be used to treat a range of cell culture products including vaccines and recombinant proteins.

The invention includes a vaccine comprising immunogenic proteins derived from a virus propagated on cell culture, wherein the vaccine is substantially free of residual functional cell culture DNA. In addition, the invention relates to recombinant proteins expressed in cell culture, where the final recombinant protein formulation is substantially free of residual functional cell culture DNA.

Functionality of any residual host cell DNA may be eliminated by treatment of the DNA with an alkylating agent which cleaves the DNA into portions small enough so that it is unable to code for a functional protein, to be transposed into a human recipient's chromosome, or otherwise be recognized by recipient DNA replication machinery. The length of degraded (non-functional) residual cell culture DNA is preferably less than 1000 base pairs (e.g. less than 1000, 800, 700, 600, 500, 400, 300, 200, 150, 100, 75, or 50 base pairs). Preferably, the length of degraded residual cell culture DNA is less than 500 base pairs. More preferably, the length of degraded residual cell culture DNA is less than 200 base pairs.

As used herein, reference to "functional DNA" or "functional RNA" indicates a nucleotide sequence capable of being translated into a functional protein or transposed into a mammalian chromosome. Generally, nucleotide sequences capable of being translated to a functional protein require promoter regions, start codons, stop codons, and internal coding sequences for functional proteins. Where DNA damage occurs, as from addition of an alkylating agent, many of these regions are altered or destroyed, such that translation can longer proceed or only proceeds to form an oligopeptide subunit of the intended protein.

"Degraded residual functional cell culture DNA" refers to functional DNA that cannot be translated into a functional protein or transposed into a mammalian chromosome. Preferably, "degraded residual functional DNA" has a length of less than 1000 base pairs, more preferably less than 500 base pairs, even more preferably less than 250 base pairs, and most preferably less than 100 base pairs. The length of the degraded residual functional DNA can be determined by standard techniques, including gel electrophoresis.

The invention provides for vaccine compositions and recombinant protein formulations which are substantially free of residual functional cell culture DNA. As used herein, substantially free of residual functional cell culture DNA refers to a composition or formulation where residual DNA fragments of less than 200 basepairs are detectable at less than 10 ng per 0.5 ml. The size of any residual cell culture DNA may be measured by standard techniques, including capillary gel electrophoresis and nucleic acid amplification technology.

The use of an alkylating agent such as BPL in the invention provides the additional benefit of reducing aggregation and contaminants. Vaccine formulations with reduced aggregates may also have improved immunogenicity. Immunogenicity of a vaccine relies upon specificity of antibodies for particular viral epitopes. If the surface of a protein is bound or masked by unwanted molecules or hidden through aggregation in large macromolecules, the epitopes may become less recognizable and therefore less efficacious in a vaccine. In addition, vaccine formulations with reduced aggregates may have additional processing advantages. Purification processes rely upon isolation of the expected protein, for example hemagglutinin and neuraminidase in an influenza vaccine. If the protein is structurally modified by the presence of aggregates or cross-linking it may not be recognized and subsequently removed by column chromatography, filtration, or centrifugation.

Alkylating Agents

Alkylating agents for use in the invention include substances that introduce an alkyl radical into a compound. Preferably, the alkylating agent is a monoalkylating agent, such as BPL. BPL is a monoalkylating agent widely used for inactivation of viruses in the preparation of many vaccines. BPL reacts with various biological molecules including nucleic acids where it causes structural modification by alkylation and depurination. BPL is generally represented by the following structure:

In vitro, BPL generally reacts with nucleophiles present in high concentrations, under conditions favorable to nucleophilic substitution reactions—as in high heat, high BPL concentrations, and aprotic polar solvents—to form functionalized propionic acids, such as 7-(2-carboxyethyl)guanine or 1-(2-carboxyethyl)deoxyadenosine (Scheme 1). Boutwell et al. Annals New York Academy of Sciences, 751-764; Perrin et al. Biologicals, 23 (1995) 207-211; Chen et al. Carcinogenesis, 2(2) (1981) 73-80.

Scheme 1 (from Chen et al.):

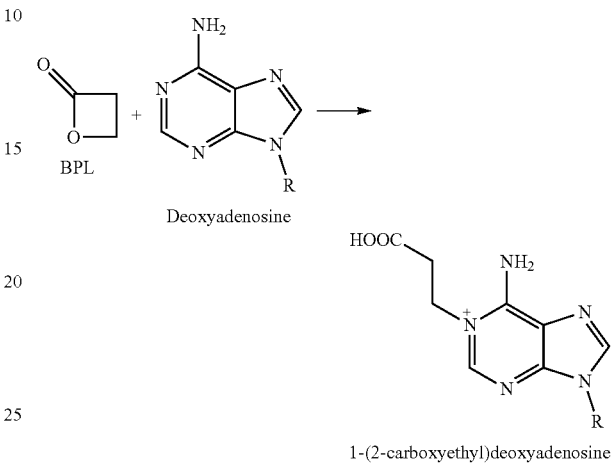

Such binding or alkylating of DNA bases induces mutagenicity by a number of mechanisms including base pair substitutions, especially depurination, deletions, and cross linking of nucleosides. The high degree of mutagenicity and reactivity of BPL corresponds to rapid viral killing and subsequent DNA degradation to non-carcinogenic by-products.

Any residual functional cell culture DNA is degraded by treatment with less than 1% BPL (e.g. less than 1%, 0.75%, 0.5%, 0.25%, 0.2%, 0.1%, 0.075%, 0.05%, 0.025%, 0.01%, or 0.005%). Preferably, residual functional cell culture DNA is degraded by treatment with between 0.1% and 0.01% BPL.

The alkylating agent is preferably added to a buffered solution and the pH of the solution is preferably maintained between 5 and 10. More preferably the pH of the solution is maintained between 6 and 9. Even more preferably the pH of the solution is maintained between 7 and 8.

In some methods, the alkylating agent is added more than once. For instance, a first BPL treatment may be performed and then a second BPL treatment may be performed. Between the first and second treatments there may be an alkylating agent removal step, but the alkylating agent may be added for the second treatment without removing any alkylating agent remaining from the first treatment.

Preferably, the alkylating agent is also used as the inactivating agent for the virus used in the vaccine. The alkylating agents of the invention are preferred over traditional inactivating agents, such as formaldehyde, which can cross-link proteins to other material, including host cell DNA. Such cross-linking can lead to the formation of aggregates (such as protein-protein conglomerates, nucleotide combinations, and protein-nucleotide combinations). Because alkylating agents, such as BPL, do not rely on such cross-linking mechanisms for viral inactivation, use of such alkylating agents for viral inactivation minimizes the formation of aggregates and other impurities in the vaccine product. Such aggregates may comprises proteins ionically or covalently bound to other proteins, proteins ionically or covalently bound to other nucleotides, and/or nucleotides ionically or covalently bound to other nucleotides.

As used herein, reference to "aggregation" or "an aggregate" indicates a mass or body of individual units or particles bound together to create larger groups or particles. Aggregation can be generally be determined by quantitative measurements of the desired components before and after a possible aggregating step or before and after application of an aggregate-disrupting method (e.g. by detergent treatment), by gel electrophoresis (such as Laemmli's system), chromatography, solution turbidity, or sedimentation studies and other methods well known in the art.

Treatment with the alkylating agent, particularly with BPL, may involve phases with different temperatures. For instance, there may be a first phase at a low temperature (e.g. at between 2-8° C., such as about 4° C.) and a second phase at a higher temperature, typically at least 10° C. higher than the first phase (e.g. at between 25-50° C., such as about 37° C.). This two-phase process is particularly useful where the alkylating agent is being used for both inactivation and DNA degradation. In a typical scheme, virus inactivation occurs during the lower temperature phase, and DNA degradation occurs during the higher temperature phase. As described in more detail below, an increased temperature can also facilitate removal of a heat-sensitive alkylating reagent.

Immunogenic Proteins

Immunogenic proteins suitable for use in the invention may be derived from any virus which is the target of a vaccine. The immunogenic proteins may be formulated as inactivated (or killed) virus, attenuated virus, split virus formulations, purified subunit formulations, viral proteins which are isolated, purified or derived from a virus, and virus like particles (VLPs).

The immunogenic proteins of the invention are viral antigens which preferably include epitopes which are exposed on the surface of the virus during at least one stage of its life cycle. The viral antigens are preferably conserved across multiple serotypes or isolates. The viral antigens include antigens derived from one or more of the viruses set forth below as well as the specific antigens examples identified below. Viruses may be non-enveloped or, preferably, enveloped. Viruses are preferably RNA viruses, and more preferably ssRNA viruses. They may have a sense or, preferably, an antisense genome. Their genomes may be non-segmented or, preferably, segmented.

*Orthomyxovirus*: Viral antigens may be derived from an *Orthomyxovirus*, such as *Influenza* A, B and C. *Orthomyxovirus* antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause pandemic a pandemic outbreak (i.e., influenza strains with new hemagglutinin compared to a hemagglutinin in currently circulating strains, or influenza strains which are pathogenic in avian subjects and have the potential to be transmitted horizontally in the human population, or influenza strains which are pathogenic to humans). Depending on the particular season and on the nature of the antigen included in the vaccine, the influenza antigens may be derived from one or more of the following hemagglutinin subtypes: H1, H2, H3, H4, H5, H6, H7, H8, H9, H10, H11, H12, H13, H14, H15 or H16.

The influenza antigens of the invention may be derived from an avian influenza strain, particularly a highly pathogenic avian influenza strain (HPAI). Alexander, *Avian Dis* (2003) 47(3 Suppl):976-81).

Further details of influenza virus antigens are given below.

*Paramyxoviridae* viruses: Viral antigens may be derived from *Paramyxoviridae* viruses, such as *Pneumoviruses* (RSV), *Paramyxoviruses* (PIV) and *Morbilliviruses* (Measles).

*Pneumovirus*: Viral antigens may be derived from a *Pneumovirus*, such as Respiratory syncytial virus (RSV), Bovine respiratory syncytial virus, *Pneumonia* virus of mice, and Turkey *Rhinotracheitis* virus. Preferably, the *Pneumovirus* is RSV. *Pneumovirus* antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred *Pneumovirus* antigens include F, G and M. See e.g., *J Gen Virol.* 2004 November; 85(Pt 11):3229). *Pneumovirus* antigens may also be formulated in or derived from chimeric viruses. For example, chimeric RSV/PIV viruses may comprise components of both RSV and PIV.

*Paramyxovirus*: Viral antigens may be derived from a *Paramyxovirus*, such as *Parainfluenza* virus types 1-4 (PIV), Mumps, Sendai viruses, Simian virus 5, Bovine parainfluenza virus and Newcastle disease virus. Preferably, the *Paramyxovirus* is PIV or Mumps. *Paramyxovirus* antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Preferred *Paramyxovirus* proteins include HN, F1 and F2. *Paramyxovirus* antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

*Morbillivirus*: Viral antigens may be derived from a *Morbillivirus*, such as Measles. *Morbillivirus* antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

*Picornavirus*: Viral antigens may be derived from *Picornaviruses*, such as *Enteroviruses, Rhinoviruses, Heparnavirus, Cardioviruses* and *Aphthoviruses*. Antigens derived from *Enteroviruses*, such as *Poliovirus* are preferred.

*Enterovirus*: Viral antigens may be derived from an *Enterovirus*, such as *Poliovirus* types 1, 2 or 3, *Coxsackie* A virus types 1 to 22 and 24, *Coxsackie* B virus types 1 to 6, *Echovirus* (ECHO) virus) types 1 to 9, 11 to 27 and 29 to 34 and *Enterovirus* 68 to 71. Preferably, the *Enterovirus* is *Poliovirus*. *Enterovirus* antigens are preferably selected from one or more of the following Capsid proteins VP1, VP2, VP3 and VP4. Commercially available polio vaccines include Inactivated Polio Vaccine (IPV) and Oral poliovirus vaccine (OPV).

*Heparnavirus*: Viral antigens may be derived from an *Heparnavirus*, such as *Hepatitis* A virus (HAV). Commercially available HAV vaccines include inactivated HAV vaccine.

*Togavirus*: Viral antigens may be derived from a *Togavirus*, such as a *Rubivirus*, an *Alphavirus*, or an *Arterivirus*. Antigens derived from *Rubivirus*, such as Rubella virus, are preferred. *Togavirus* antigens may be selected from E1, E2, E3, C, NSP-1, NSPO-2, NSP-3 or NSP-4. *Togavirus* antigens are preferably selected from E1, E2 or E3. Commercially available Rubella vaccines include a live cold-adapted virus, typically in combination with mumps and measles vaccines (MMR).

*Flavivirus*: Viral antigens may be derived from a *Flavivirus*, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, *Powassan encephalitis*. *Flavivirus* antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

*Pestivirus*: Viral antigens may be derived from a *Pestivirus*, such as Bovine viral diarrhea (BVDV), Classical swine fever (CSFV) or Border disease (BDV).

*Hepadnavirus*: Viral antigens may be derived from a *Hepadnavirus*, such as *Hepatitis* B virus. *Hepadnavirus* antigens may be selected from surface antigens (L, M and S), core antigens (HBc, HBe). Commercially available HBV vaccines include subunit vaccines comprising the surface antigen S protein.

*Hepatitis* C virus: Viral antigens may be derived from a *Hepatitis* C virus (HCV). HCV antigens may be selected from one or more of E1, E2, E1/E2, NS345 polyprotein, NS 345-core polyprotein, core, and/or peptides from the non-structural regions (Houghton et al., *Hepatology* (1991) 14:381).

*Rhabdovirus*: Viral antigens may be derived from a *Rhabdovirus*, such as a *Lyssavirus* (Rabies virus) and *Vesiculovirus* (VSV). *Rhabdovirus* antigens may be selected from glycoprotein (G), nucleoprotein (N), large protein (L), non-structural proteins (NS). Commercially available Rabies virus vaccine comprise killed virus grown on human diploid cells or fetal rhesus lung cells.

*Caliciviridae*; Viral antigens may be derived from *Caliciviridae*, such as Norwalk virus, and Norwalk-like Viruses, such as Hawaii Virus and Snow Mountain Virus.

*Coronavirus*: Viral antigens may be derived from a *Coronavirus*, SARS, Human respiratory coronavirus, Avian infectious bronchitis (TRV), Mouse hepatitis virus (MHV), and Porcine transmissible gastroenteritis virus (TGEV). *Coronavirus* antigens may be selected from spike (S), envelope (E), matrix (M), nucleocapsid (N), and Hemagglutinin-esterase glycoprotein (HE). Preferably, the *Coronavirus* antigen is derived from a SARS virus. SARS viral antigens are described in WO 04/92360.

*Retrovirus*: Viral antigens may be derived from a *Retrovirus*, such as an *Oncovirus*, a *Lentivirus* or a *Spumavirus*. Oncovirus antigens may be derived from HTLV-1, HTLV-2 or HTLV-5. *Lentivirus* antigens may be derived from HIV-1 or HIV-2. *Retrovirus* antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$.

*Reovirus*: Viral antigens may be derived from a *Reovirus*, such as an *Orthoreovirus*, a *Rotavirus*, an *Orbivirus*, or a *Coltivirus*. *Reovirus* antigens may be selected from structural proteins $\lambda 1$, $\lambda 2$, $\lambda 3$, $\mu 1$, $\mu 2$, $\sigma 1$, $\sigma 2$, or $\sigma 3$, or nonstructural proteins $\sigma NS$, $\mu NS$, or $\sigma 1s$. Preferred Reovirus antigens may be derived from a *Rotavirus*. Rotavirus antigens may be selected from VP1, VP2, VP3, VP4 (or the cleaved product VP5 and VP8), NSP 1, VP6, NSP3, NSP2, VP7, NSP4, or NSP5. Preferred *Rotavirus* antigens include VP4 (or the cleaved product VP5 and VP8), and VP7.

*Parvovirus*: Viral antigens may be derived from a *Parvovirus*, such as *Parvovirus* B19. *Parvovirus* antigens may be selected from VP-1, VP-2, VP-3, NS-1 and NS-2. Preferably, the *Parvovirus* antigen is capsid protein VP-2.

*Delta hepatitis* virus (HDV): Viral antigens may be derived HDV, particularly $\delta$-antigen from HDV (see, e.g., U.S. Pat. No. 5,378,814).

*Hepatitis* E virus (HEV): Viral antigens may be derived from HEV.

*Hepatitis* G virus (HGV): Viral antigens may be derived from HGV.

*Human Herpesvirus*: Viral antigens may be derived from a *Human Herpesvirus*, such as *Herpes Simplex* Viruses (HSV), *Varicella-zoster* virus (VZV), *Epstein-Barr* virus (EBV), *Cytomegalovirus* (CMV), *Human Herpesvirus* 6 (HHV6), *Human Herpesvirus* 7 (HHV7), and *Human Herpesvirus* 8 (HHV8). *Human Herpesvirus* antigens may be selected from immediate early proteins ($\alpha$), early proteins ($\beta$) and late proteins ($\gamma$). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins.

*Papovaviruses*: Antigens may be derived from *Papovaviruses*, such as *Papillomaviruses* and *Polyomaviruses*. *Papillomaviruses* include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). *Polyomyavirus* viruses include BK virus and JK virus. *Polyomavirus* antigens may be selected from VP1, VP2 or VP3.

Further provided are viral antigens described in *Vaccines*, $4^{th}$ Edition (Plotkin and Orenstein ed. 2004); *Medical Microbiology* $4^{th}$ Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the compositions of the present invention.

Immunogenic proteins suitable for use in the invention may be derived from a virus which causes respiratory disease. Examples of such respiratory antigens include proteins derived from a respiratory virus such as *Orthomyxoviruses* (influenza), *Pneumovirus* (RSV), *Paramyxovirus* (PIV), *Morbillivirus* (measles), *Togavirus* (Rubella), VZV, and *Coronavirus* (SARS). Immunogenic proteins derived from influenza virus are particularly preferred.

The compositions of the invention may include one or more immunogenic proteins suitable for use in pediatric subjects. Pediatric subjects are typically less than about 3 years old, or less than about 2 years old, or less than about 1 years old. Pediatric antigens may be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of *Orthomyxovirus* (influenza), *Pneumovirus* (RSV), *Paramyxovirus* (PIV and Mumps), *Morbillivirus* (measles), *Togavirus* (Rubella), *Enterovirus* (polio), HBV, *Coronavirus* (SARS), and *Varicella-zoster* virus (VZV), *Epstein Barr* virus (EBV).

The compositions of the invention may include one or more immunogenic proteins suitable for use in elderly or immunocompromized individuals. Such individuals may need to be vaccinated more frequently, with higher doses or with adjuvanted formulations to improve their immune response to the targeted antigens. Antigens which may be targeted for use in Elderly or Immunocompromized individuals include antigens derived from one or more of the following viruses: *Orthomyxovirus* (influenza), *Pneumovirus* (RSV), *Paramyxovirus* (PIV and Mumps), *Morbillivirus* (measles), *Togavirus* (Rubella), *Enterovirus* (polio), HBV, *Coronavirus* (SARS), *Varicella-zoster* virus (VZV), *Epstein Barr* virus (EBV), and *Cytomegalovirus* (CMV).

After growing viruses, the aklylating agent may be used on purified virions e.g. on virions present in a clarified cell culture, or on virions purified from such a clarified cell culture. A method of the invention may involve removing cellular material by clarification, and then purification of virions from the clarified cell culture e.g. by chromatography. The alkylating agent maybe used on virions purified in this manner, or after a further optional step of ultrafiltration/diafiltration. Preferred methods use the aklylating agent not on the clarified supernatant of an infected cell culture, but on virions purified from such a clarified supernatant (cf. Morgeaux et al. (1993) *Vaccine* 11:82-90).

The aklylating agent is preferably used after a step of endotoxin removal has taken place.

Method Steps

The vaccine compositions of the invention may be prepared by isolation of the immunogenic protein and degradation of residual functional host cell DNA. Similarly, recombinant protein formulations may be prepared by isolation or purification of the recombinant protein and degradation of residual functional host cell DNA. These steps may be carried out sequentially or simultaneously. The step of degrading residual functional cell culture DNA is done by addition of an alkylating agent e.g. BPL.

The alkylating agent and any residual side products are preferably removed prior to the final formulation of the vaccine or recombinant protein. Preferably, the vaccine composition or recombinant protein formulation contains less than 0.1% free propionic acid and BPL combined (e.g. less than 0.1%, 0.05%, 0.025%, 0.01%, 0.005%, 0.001%, or 0.01%. Preferably, the final vaccine composition or recombinant protein formulation contains less than 0.01% BPL.

BPL can conveniently be removed by heating, to cause hydrolysis into the non-toxic β-hydroxypropionic acid. The length of time required for hydrolysis depends on the total amount of BPL and the temperature. Higher temperatures given more rapid hydrolysis, but the temperature should not be raized so high as to damage the active proteinaceous ingredients. As described below, heating to about 37° C. for 2-2.5 hours is suitable for removing BPL.

After treatment of DNA, the residual DNA products may be retained in the final immunogenic or recombinant composition. More preferably, however, they are separated from desired components e.g. separated from virions/proteins. Separation in this way may remove DNA degradation products in part or in full, and preferably removes any degraded DNA that is >200 bp. Thus a method of the invention may include a step of separating DNA from virions. This separation step may involve e.g. one or more of ultrafiltration, ultracentrifugation (including gradient ultracentrifugation), virus core pelleting and supernatant fractionation, chromatography (such as ion exchange chromatography e.g. anion exchange), adsorption, etc.

Overall, therefore, a method may involve treatment with an alkylating agent to degrade the length of residual DNA, and later purification to remove residual DNA (including removal of degraded DNA).

Cell Culture

Vaccines of the invention are prepared from viruses which are propagated on cell culture. In addition, the invention includes formulations of recombinant proteins expressed in cell culture. Mammalian cell cultures are preferred for both viral replication and recombinant protein expression.

A number of mammalian cell lines are known in the art and include cell lines derived from human or non-human primate (e.g. monkey) cells (e.g. PER.C6 cells which are described, for example, in WO01/38362, WO01/41814, WO02/40665, WO2004/056979, and WO2005/080556, incorporated by reference herein in their entireties, as well as deposited under ECACC deposit number 96022940), MRC-5 (ATCC CCL-171), WI-38 (ATCC CCL-75), HEK cells, HeLa cells, fetal rhesus lung cells (ATCC CL-160), human embryonic kidney cells (293 cells, typically transformed by sheared adenovirus type 5 DNA), Vero cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO 97/37000 and WO 97/37001), cat, and rodent (e.g. hamster cells, such as BHK21-F, HKCC cells, or Chinese hamster ovary (CHO) cells), and may be obtained from a wide variety of developmental stages, including for example, adult, neonatal, fetal, and embryo.

Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. The use of mammalian cells means that vaccines can be free from materials such as chicken DNA, egg proteins (such as ovalbumin and ovomucoid), etc., thereby reducing allergenicity.

In certain embodiments the cells are immortalized (e.g. PER.C6 cells; ECACC 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal or kidney cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinal cells or retinoblasts, lung cells, and stromal cells.

WO97/37000 and WO97/37001 describe production of animal cells and cell lines that capable of growth in suspension and in serum free media and are useful in the production and replication of viruses, particularly influenza virus. Further details are given in WO03/023021 and WO03/023025.

Preferred mammalian cell lines for growing influenza viruses include: MDCK cells, derived from Madin Darby canine kidney; Vero cells, derived from African green monkey (*Cercopithecus aethiops*) kidney; or PER.C6 cells, derived from human embryonic retinoblasts. These cell lines are widely available e.g. from the American Type Cell Culture (ATCC) collection, from the Coriell Cell Repositories, or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940.

The most preferred cell lines for growing influenza viruses are MDCK cell lines. The original MDCK cell line is available from the ATCC as CCL-34, but derivatives of this cell line may also be used. For instance, WO97/37000 discloses a MDCK cell line that was adapted for growth in suspension culture ('MDCK 33016', deposited as DSM ACC 2219). Similarly, EP-A-1260581 (WO01/64846) discloses a MDCK-derived cell line that grows in suspension in serum-free culture ('B-702', deposited as FERM BP-7449). WO2006/071563 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). WO2005/113758 discloses MDCK cell lines with high susceptibility to infection, including 'MDCK.5F1' cells (ATCC CRL-12042). Any of these MDCK cell lines can be used.

Manipulation of MDCK cell cultures in suspension and adherent cultures is described in WO97/37000, WO97/37001, WO03/023021, and WO03/023025. In particular, WO 03/023021 and WO 03/023025 describe laboratory and commercial scale cell culture volumes of MDCK suspension cells in serum-free media, chemically defined media, and protein free media. Each reference is incorporated herein in its entirety.

As an alternative to mammalian sources, cell lines for use in the invention may be derived from avian sources such as chicken, duck, goose, quail or pheasant. Avian cell lines may be derived from a variety of developmental stages including embryonic, chick and adult. Preferably, the cell lines are derived from the embryonic cells, such as embryonic fibroblasts, germ cells, or individual organs, including neuronal, brain, retina, kidney, liver, heart, muscle, or extraembryonic tissues and membranes protecting the embryo. Examples of avian cell lines include avian embryonic stem cells (WO01/85938 and WO03/076601) and duck retina cells (WO2005/042728). Suitable avian embryonic stem cells, include the EBx cell line derived from chicken embryonic stem cells, EB45, EB14, and EB14-074 (WO2006/108846). Chicken embryo fibroblasts (CEF) may also be used. These avian cells are particularly suitable for growing influenza viruses.

Insect cell expression systems, such as baculovirus recombinant expression systems, are known to those of skill in the art and described in, e.g., Summers and Smith, *Texas Agricultural Experiment Station Bulletin* No. 1555 (1987). Materials and methods for baculovirus/insert cell expression systems are commercially available in kit form from, inter alia, Invitrogen, San Diego Calif. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Recombinant expression of proteins may also be conducted in bacterial hosts such as *Escherichia coli, Bacillus subtilis*, and *Streptococcus* spp. Yeast hosts suitable for recombinant expression of proteins include *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaceharomyces pombe* and *Yarrowia lipolytica*.

Culture conditions for the above cell types are well-described in a variety of publications, or alternatively culture medium, supplements, and conditions may be purchased commercially, such as for example, as described in the catalog and additional literature of Cambrex Bioproducts (East Rutherford, N.J.).

In certain embodiments, the host cells used in the methods described herein are cultured in serum free and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Known serum-free media include Iscove's medium, Ultra-CHO medium (Bio Whittaker) or EX-CELL (JRH Bioscience). Ordinary serum-containing media include Eagle's Basal Medium (BME) or Minimum Essential Medium (MEM) (Eagle, Science, 130, 432 (1959)) or Dulbecco's Modified Eagle Medium (DMEM or EDM), which are ordinarily used with up to 10% fetal calf serum or similar additives. Optionally, Minimum Essential Medium (MEM) (Eagle, Science, 130, 432 (1959)) or Dulbecco's Modified Eagle Medium (DMEM or EDM) may be used without any serum containing supplement. Protein-free media like PF-CHO (JHR Bioscience), chemically-defined media like ProCHO 4CDM (Bio Whittaker) or SMIF 7 (Gibco/BRL Life Technologies) and mitogenic peptides like Primactone or Pepticase (all from Quest International) or lactalbumin hydrolyzate (Gibco and other manufacturers) are also adequately known in the prior art. The media additives based on plant hydrolyzates have the special advantage that contamination with viruses, mycoplasma or unknown infectious agents can be ruled out.

Cell culture conditions (temperature, cell density, pH value, etc.) are variable over a very wide range owing to the suitability of the cell line employed according to the invention and can be adapted to the requirements of particular virus growth conditions or recombinant expression details.

Cells may be grown in various ways e.g. in suspension, in adherent culture, on microcarriers.

Cells may be grown below 37° C. (e.g. 30-36° C.) during viral replication (WO97/37001).

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells may be inoculated with a virus (measured by PFU or $TCID_{50}$) to cell ratio of 1:500 to 1:1, preferably 1:100 to 1:5, more preferably 1:50 to 1:10. The virus can be added to a suspension of the cells or applied to a monolayer of the cells, and the virus is absorbed on the cells for at least 60 minutes but usually less than 300 minutes, preferably between 90 and 240 minutes at 25° C. to 40° C., preferably 28° C. to 37° C.

The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

The vaccine compositions of the invention will generally be formulated in a sub-virion form e.g. in the form of a split virus, where the viral lipid envelope has been dissolved or disrupted, or in the form of one or more purified viral proteins. The vaccine composition will contain a sufficient amount of the antigen(s) to produce an immunological response in the patient.

Methods of splitting viruses, such as influenza viruses, are well known in the art e.g. see WO02/28422, WO02/067983, WO02/074336, WO01/21151, etc. Splitting of the virus is carried out by disrupting or fragmenting whole virus, whether infectious (wild-type or attenuated) or non-infectious (e.g. inactivated), with a disrupting concentration of a splitting agent. Splitting agents generally include agents capable of breaking up and dissolving lipid membranes, typically with a hydrophobic tail attached to a hydrophilic head. The most preferred splitting agent is cetyltrimethylammoniumbromide (CTAB). Further details of splitting are given below in the context: of influenza viruses.

The disruption results in a full or partial solubilization of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethylene esters, etc.

Methods of purifying individual proteins from viruses are well known and include, for example, filtration, chromatography, centrifugation steps and hollow fiber elution. In one embodiment, the proteins are purified by ion exchange resin.

As a further alternative, the vaccine may include a whole virus e.g. a live attenuated whole virus or, preferably, an inactivated whole virus. Methods of inactivating or killing viruses to destroy their ability to infect mammalian cells are known in the art. Such methods include both chemical and physical means. Chemical means for inactivating a virus include treatment with an effective amount of one or more of the following agents: detergents, formaldehyde, formalin, BPL, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. Preferably, the virus is inactivated with BPL.

Pharmaceutical Compositions

Compositions of the invention are pharmaceutically acceptable. They usually include components in addition to the antigens e.g. they typically include one or more pharmaceutical carrier(s) and/or excipient(s). A thorough discussion of such components is available in *Remington: The Science and Practice of Pharmacy* (Gennaro, 2000; 20th edition, ISBN: 0683306472).

Compositions will generally be in aqueous form.

The composition may include one or more preservatives, such as thiomersal or 2-phenoxyethanol. It is preferred, however, that the vaccine should be substantially free from (i.e. less than 5 μg/ml) mercurial material e.g. thiomersal-free (Banzhoff (2000) *Immunology Letters* 71:91-96; WO02/097072). Vaccines containing no mercury are more preferred. Preservative-free vaccines are particularly preferred.

It is preferred to include a physiological salt, such as a sodium salt e.g. to control tonicity. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5. A method of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

Compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate. The detergent may be present only at trace amounts.

The composition may include material for a single immunization, or may include material for multiple immunizations (i.e. a 'multidose' kit). The inclusion of a preservative is useful in multidose arrangements. As an alternative (or in addition) to including a preservative in multidose compositions, the compositions may be contained in a container having an aseptic adaptor for removal of material.

Vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Methods of Treatment, and Administration of Vaccines

Compositions of the invention are suitable for administration to animal (and, in particular, human) patients, and the invention provides a method of raising an immune response in a patient, comprising the step of administering a composition of the invention to the patient.

The invention also provides a kit or composition of the invention for use as a medicament.

The invention also provides the use of immunogenic proteins derived from a virus propagated on cell culture, wherein said vaccine is substantially free of residual functional cell culture DNA, in the manufacture of a medicament for raising an immune response in a patient.

The immune response raized by these methods and uses will generally include an antibody response, preferably a protective antibody response. Methods for assessing antibody responses, neutralizing capability and protection after viral vaccination are well known in the art. For influenza virus, for instance, human studies have shown that antibody titers against HA are correlated with protection (a serum sample hemagglutination-inhibition titer of about 30-40 gives around 50% protection from infection by a homologous virus) [Potter & Oxford (1979) *Br Med Bull* 35: 69-75].

Compositions of the invention can be administered in various ways. The most preferred immunization route is by intramuscular injection (e.g. into the arm or leg), but other available routes include subcutaneous injection, intranasal, oral, intradermal, transcutaneous, transdermal, etc.

Vaccines prepared according to the invention may be used to treat both children and adults. The patient may be less than 1 year old, 1-5 years old, 5-15 years old, 15-55 years old, or at least 55 years old. Patients may be elderly (e.g. ≥50 years old, ≥60 years old, and preferably ≥65 years), the young (e.g. ≤5 years old), hospitalized patients, healthcare workers, armed service and military personnel, pregnant women, the chronically ill, immunodeficient patients, patients who have taken an antiviral compound (e.g. an oseltamivir or zanamivir compound for influenza; see below) in the 7 days prior to receiving the vaccine, people with egg allergies and people travelling abroad. The vaccines are not suitable solely for these groups, however, and may be used more generally in a population.

Treatment can be by a single dose schedule or a multiple dose schedule. Multiple doses may be used in a primary immunization schedule and/or in a booster immunization schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a bacterial vaccine, such as a diphtheria vaccine, a tetanus vaccine, a pertussis vaccine, a DTP vaccine, a conjugated *H. influenzae* type b vaccine, a meningococcal conjugate vaccine (such as a tetravalent A-C-W135-Y vaccine), a pneumococcal conjugate vaccine, etc.

Similarly, vaccines of the invention may be administered to patients at substantially the same time as (e.g. during the same medical consultation or visit to a healthcare professional) an antiviral compound effective against the virus of the vaccine. Where the vaccine is an influenza vaccine, for instance, the compound(s) may be a neuraminidase inhibitor (e.g. oseltamivir and/or zanamivir). These antivirals include a (3R,4R,5S)-4-acetylamino-5-amino-3(1-ethylpropoxy)-1-cyclohexene-1-carboxylic acid or a 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral effective against influenza is (3R,4R,5S)-4-acetylamino-5-amino-3(1-ethylpropoxy)-1-cyclohexene-1-carboxylic acid, ethyl ester, phosphate (1:1), also known as oseltamivir phosphate.

Host Cell DNA

Measurement of residual host cell DNA is within the normal capabilities of the skilled person. The total amount of residual DNA in compositions of the invention is preferably less than 20 ng/ml e.g. ≤10 ng/ml, ≤5 ng/ml, ≤1 ng/ml, ≤100 pg/ml, ≤10 pg/ml, etc. As described above, substantially all of this DNA is preferably less than 500 base pairs in length.

The assay used to measure DNA will typically be a validated assay (*Guidance for Industry: Bioanalytical Method Validation*. U.S. Department of Health and Human Services Food and Drug Administration Center for Drug Evaluation and Research (CDER) Center for Veterinary Medicine (CVM). May 2001; Lundblad (2001) *Biotechnology and Applied Biochemistry* 34:195-197). The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots (Ji et al. (2002) *Biotechniques*. 32:1162-7); immunoassay methods, such as the system disclosed in Briggs (Briggs (1991) *J Parenter Sci Technol*. 45:7-12; and quantitative PCR (Lahijani et al. (1998) *Hum Gene Ther*. 9:1173-80). These methods are all familiar to the skilled person, although the precise characteristics of each method may depend on the host cell in question e.g. the choice of probes for hybridization, the choice of primers and/or probes for amplification, etc. The system from Molecular Devices is a quantitative assay for picogram levels of total DNA, and has been used for monitoring levels of contaminating DNA in biopharmaceuticals (Briggs (1991) supra). A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. Althea Technologies, etc. A comparison of a chemiluminescent hybridization assay and the total DNA system for measuring host cell DNA contamination of a human viral vaccine can be found in Lokteff et al. (2001) *Biologicals*. 29:123-32.

These various analytical methods may also be used for measuring the length of residual host cell DNA. As mentioned above, the average length of residual host cell DNA, after treatment with the alkylating agent, is preferably less than 500 base pairs, or even less than 200 base pairs.

In relation to canine cells in particular, such as MDCK cells, analysis of the genome reveals 13 coding sequences <500 bp in length, 3 sequences <200 bp and 1 sequence <100 bp. Thus fragmentation of DNA to <200 bp removes substantially all coding sequences, and it is highly unlikely that any fragment would actually correspond to one of the 3 genes around that length (namely: secretin at 81 bp; PYY at 108 bp; and osteocalcin at 135 bp).

Adjuvants

Compositions of the invention may include an adjuvant, which can function to enhance the immune responses (humoral and/or cellular) elicited in a patient who receives the composition. The use of adjuvants with viral vaccines is well known e.g. in hepatitis vaccines, polio vaccines, etc.

Adjuvants that can be used with the invention include, but are not limited to, aluminum salts, immunostimulatory oligonucleotides, saponins, lipid A analogs (such as 3dMPL) and oil-in-water emulsions. These and other adjuvants are disclosed in more detail in Powell & Newman (*Vaccine Design: The Subunit and Adjuvant Approach*, Plenum Press 1995, ISBN 0-306-44867-X) and O'Hagan (*Vaccine Adjuvants: Preparation Methods and Research Protocols*, volume 42 of *Methods in Molecular Medicine series*, ISBN: 1-59259-083-7).

The adjuvants known as aluminum hydroxide and aluminum phosphate may be used. These names are conventional, but are used for convenience only, as neither is a precise description of the actual chemical compound which is present (e.g. see chapter 9 of Powell & Newman). The invention can use any of the "hydroxide" or "phosphate" adjuvants that are in general use as adjuvants. Adsorption to these salts is preferred.

Immunostimulatory oligonucleotides with adjuvant activity are well known. They may contain a CpG motif (a dinucleotide sequence containing an unmethylated cytosine linked by a phosphate bond to a guanosine), a TpG motif, an oligo-dT sequence, an oligo-dC sequence, double-stranded RNA, palindromic sequences, a poly(dG) sequence, etc. Immunostimulatory oligonucleotides will typically comprise at least 20 nucleotides, and may comprise fewer than 100 nucleotides.

Saponins (chapter 22 of Powell & Newman) are a heterologous group of sterol glycosides and triterpenoid glycosides that are found in the bark, leaves, stems, roots and even flowers of a wide range of plant species. Saponins from the bark of the *Quillaia saponaria* Molina tree have been widely studied as adjuvants. Saponin adjuvant formulations include purified formulations, such as QS21, as well as lipid formulations, such as ISCOMs. Saponin compositions have been purified using HPLC and RP-HPLC, and specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (WO96/33739). Combinations of saponins and cholesterols can be used to form unique particles called immunostimulating complexes (ISCOMs), ISCOMs, which typically also include a phospholipid.

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. 3dMPL can take the form of a mixture of related molecules, varying by their acylation (e.g. having 3, 4, 5 or 6 acyl chains, which may be of different lengths).

Various oil-in-water emulsions with adjuvant activity are known. They typically include at least one oil and at least one surfactant, with the oil(s) and surfactant(s) being biodegradable (metabolisable) and biocompatible. The oil droplets in the emulsion generally have sub-micron diameters, with these small sizes being achieved with a microfluidiser to provide stable emulsions. Droplets with a size less than 220 nm are preferred as they can be subjected to filter sterilization.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59', as described in more detail in Chapter 10 of Powell & Newman and chapter 12 of O'Hagan. The MF59 emulsion advantageously includes citrate ions e.g. 10 mM sodium citrate buffer.

An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL. The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 m/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL. The aqueous phase may contain a phosphate buffer.

Influenza Vaccines

The invention is particularly suitable for preparing influenza virus vaccines. Various forms of influenza virus vaccine are currently available e.g. see chapters 17 & 18 of Plotkin & Orenstein (*Vaccines*, 4th edition, 2004, ISBN: 0-7216-9688-0). They are generally based either on live virus or on inactivated virus. Inactivated vaccines may be based on whole virions, 'split' virions, or on purified surface antigens (including hemagglutinin). Influenza antigens can also be presented in the form of virosomes (nucleic acid free viral-like liposomal particles). Antigens purified from a recombinant host (e.g. in an insect cell line using a baculovirus vector) may also be used.

Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, etc.) to produce subvirion preparations, including the 'Tween-ether' splitting process. Methods of splitting influenza viruses are well known in the art e.g. WO02/28422, WO02/067983, WO02/074336, WO01/21151, WO02/097072, WO2005/113756 etc. Splitting of the virus is typically carried out by disrupting or fragmenting whole virus, whether infectious or non-infectious with a disrupting concentration of a splitting agent. The disruption results in a full or partial solubilization of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution.

Purified surface antigen vaccines comprise the influenza surface antigens hemagglutinin and, typically, also neuraminidase. Processes for preparing these proteins in purified form are well known in the art.

Influenza virus strains for use in vaccines change from season to season. In the current inter-pandemic period, vaccines typically include two influenza A strains (H1N1 and H3N2) and one influenza B strain, and trivalent vaccines are typical. The invention may also use HA from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may protect against one or more of influenza A virus hemagglutinin subtypes H1, H2, H3, H4, H5, H6, H7, H8, H9, H10, H11, H12, H13, H14, H15 or H16.

As well as being suitable for immunizing against inter-pandemic strains, the compositions of the invention are particularly useful for immunizing against pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A virus with H5 hemagglutinin type is preferred for immunizing against pandemic influenza, such as a H5N1 strain. Other possible strains include H5N3, H9N2, H2N2, H7N1 and H7N7, and any other emerging potentially pandemic strains. Within the H5 subtype, a virus may fall into HA clade 1, HA clade 1', HA clade 2 or HA clade 3 (World Health Organization (2005) *Emerging Infectious Diseases* 11(10):1515-21), with clades 1 and 3 being particularly relevant. Other strains whose antigens can usefully be included in the compositions are strains which are resistant to antiviral therapy (e.g. resistant to oseltamivir and/or zanamivir), including resistant pandemic strains.

Compositions of the invention may include antigen(s) from one or more (e.g. 1, 2, 3, 4 or more) influenza virus strains, including influenza A virus and/or influenza B virus. A trivalent vaccine is preferred, including antigens from two influenza A virus strains and one influenza B virus strain.

The influenza virus may be a reassortant strain, and may have been obtained by reverse genetics techniques. Thus an influenza A virus may include one or more RNA segments from a A/PR/8/34 virus (typically 6 segments from A/PR/8/34, with the HA and N segments being from a vaccine strain, i.e. a 6:2 reassortant). It may also include one or more RNA segments from a A/WSN/33 virus, or from any other virus strain useful for generating reassortant viruses for vaccine preparation. Typically, the invention protects against a strain that is capable of human-to-human transmission, and so the strain's genome will usually include at least one RNA segment that originated in a mammalian (e.g. in a human) influenza virus. It may include NS segment that originated in an avian influenza virus.

HA is the main immunogen in current inactivated influenza vaccines, and vaccine doses are standardized by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 15, about 10, about 7.5, about 5, about 3.8, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

HA used with the invention may be a natural HA as found in a virus, or may have been modified. For instance, it is known to modify HA to remove determinants (e.g. hyper-basic regions around the cleavage site between HA1 and HA2) that cause a virus to be highly pathogenic in avian species.

After treating a virion-containing composition to degrade host cell DNA (e.g. with BPL), the degradation products are preferably removed from virions e.g. by anion exchange chromatography.

Once an influenza virus has been purified for a particular strain, it may be combined with viruses from other strains e.g. to make a trivalent vaccine as described above. It is preferred to treat each strain separately and to mix monovalent bulks to give a final multivalent mixture, rather than to mix viruses and degrade DNA from a multivalent mixture.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

By the terms "isolated" and "purified" is meant at least 50% pure, more preferably 60% pure (as with most split vaccines), more preferably 70% pure, or 80% pure, or 90% pure, or 95% pure, or greater than 99% pure.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

BRIEF DESCRIPTION OF THE DRAWINGS

FIGS. 1 and 2 show the results of PCR amplification of 6 named targets in the MDCK genome. Some samples were diluted as indicated, up to 1:10000, prior to PCR.

FIG. 3 shows the results of PCR amplification of SINE sequences in the MDCK genome. As in FIGS. 1 & 2, DNA was sometimes diluted prior to PCR. In the lower panel, the figures are the starting amount of DNA in the PCR (fg).

FIG. 4 shows the effect of BPL treatment on the size of MDCK DNA. Genomic DNA was incubated with BPL at different temperatures and for different lengths of time. FIG. 5 shows similar results. Agarose gels were stained with SYBRGold.

FIG. 6 shows capillary electrophoresis of residual DNA (top line) relative to markers (bottom line) having the indicated sizes.

MODES FOR CARRYING OUT THE INVENTION

Influenza viruses (A/New Caledonia/20/99(H1N1), A/Panama/2007/99(H3N2); B/Jiangsu/10/2003; A/Wyoming/3/2003(H3N2)) were grown in MDCK cells in a suspension culture, following the teaching of WO97/37000, WO03/23025 and WO04/92360. The final culture medium was clarified to provide virions, which were then subjected to chromatography and ultrafiltration/diafiltration. Virions in the resulting material were inactivated using β-propiolactone (final concentration 0.05% v/v; incubated for 16-20 hours at 2-8° C., and then hydrolyzed by incubating at 37° C. for 2-2.5 hours). CTAS was then used to split the virions, and various further processing steps gave a final monovalent bulk vaccine containing purified surface proteins.

MDCK DNA was characterized to evaluate its amount, size, and integrity at three stages of the manufacturing process: (A) after the ultrafiltration/diafiltration step; (B) after β-propiolactone treatment; and (C) in the final monovalent bulk. Capillary gel electrophoresis and nucleic acid amplification were used to investigate the size, the integrity and the biological activity of any residual genomic DNA.

Size Determination

As mentioned above, the size of residual host cell DNA was analyzed at stages (A), (B) and (C) by capillary gel electrophoresis. The analysis was performed on five separate virus cultures.

500 μl samples were removed at these three points and treated with 10 μl proteinase K at 56° C. for 16 to 22 h followed by a total DNA extraction with the DNA Extractor Kit (Wako Chemicals) following the manufacturer's instructions. DNA was resuspended in 500 μl ultra pure water for electrophoresis on a P/ACE MDQ Molecular Characterization System (Beckman Coulter) at a constant temperature of 20° C. Eleven molecular size markers were used, from 72 to 1353 bp. The nucleic acid detection limit (DL) for this method was 0.7 μg/ml.

Based on the size markers and relative density of the DNA bands, the distribution and size of the DNA fragments were determined and assigned to four different size categories between ranging from <200 bp to >1000 bp. FIG. 6 shows capillary electrophoresis of a stage (C) sample. The analysis shows that all detectable residual DNA in this sample is substantially below 200 bp in length.

Average results from the five cultures are shown in the following table:

| Stage | DNA amount | <200 bp | 200-500 bp | 500-1000 bp | >1000 bp |
|---|---|---|---|---|---|
| A | 47 mg | 25% | 12% | 6% | 55% |
| B | 5 mg | 79% | 18% | 3% | 4% |
| C | 0.07 mg | >99% | <DL | <DL | <DL |

BPL treatment thus causes a ~10-fold reduction in the amount of DNA, but also shifts the distribution away from long sequences towards small fragments <200 bp. Further processing, between steps (B) and (C), including chromatography and ultrafiltration steps, reduced total DNA levels another ~70-fold, and removed all detectable DNA ≥200 bp.

DNA Amplification

Neoplastic cell transformation is a phenomenon often associated with modified proto-oncogenes and/or modified tumor suppressor genes. Sequences from several such canine genes were analyzed by PCR before and after BPL treatment i.e. at points (A) and (B). In addition, DNA from uninfected MDCK cells was treated and tested. Proto-oncogenes tested were: H-ras and c-myc. Tumor suppressor genes tested were: p53; p21/waf-1; and PTEN. In addition, repetitive SINE sequences were analyzed by PCR. The high copy number for SINES facilitates sensitive detection.

All samples were spiked with an external control DNA (pUC19 fragment) for monitoring the quality of the sample preparation and the PCR. In all experiments a consistent amplification of the spike control was observed, indicating that residual hydrolyzed BPL and by-products present in the PCR mixtures does not have inhibitory effects on the assay and ensured a sufficient quality of sample preparation and PCR. Samples were diluted in 10-fold steps before amplification, until PCR products could not be detected, thereby indicating the log reduction in DNA levels. The detection limit for the PCR assay is 55 pg.

Figure 2:
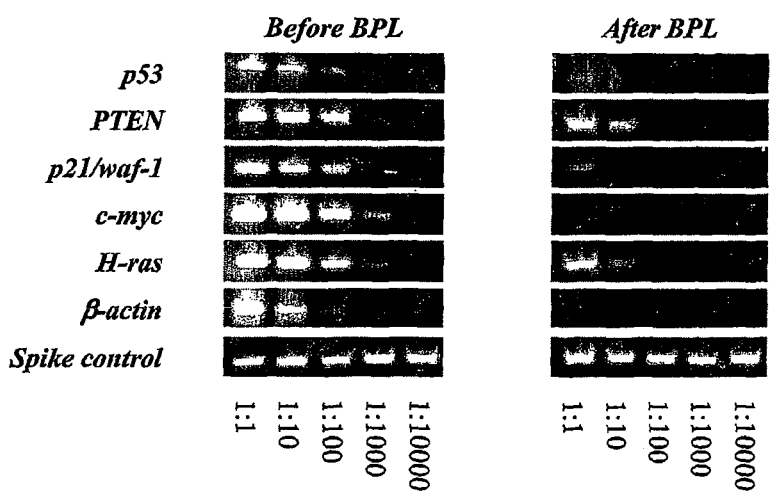

PCR products were analyzed by agarose gel electrophoresis. FIG. 1 shows results obtained in uninfected MDCK cells, and FIG. 2 shows results obtained during virus culture. All six analyzed genes showed a strong amplification signal before BPL treatment, but signal strength diminished after exposure to BPL. In all tested production lots, residual MDCK genomic DNA was decreased by at least 2 log values after BPL exposure.

Figure 3:
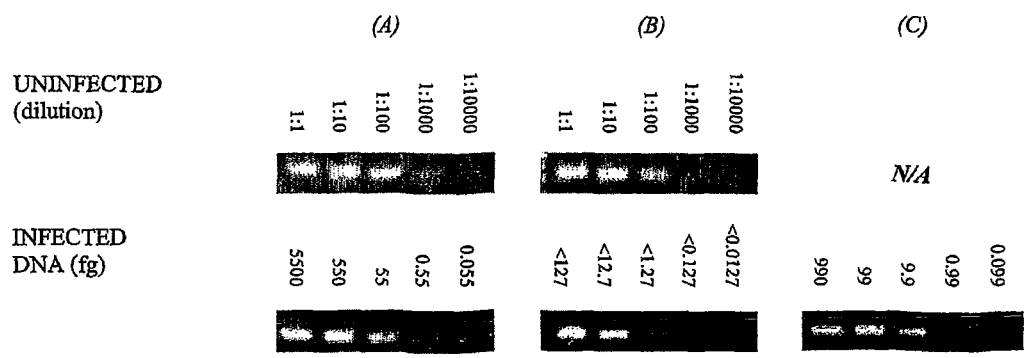

Because FIG. 2 shows results at stage (B), before further purification, the results over-represent DNA present in final bulk vaccines. Due to the sensitivity when using SINE sequences, however, PCR was also possible at stage (C), in the final monovalent bulk. Results of this analysis are shown in FIG. 3. DNA amplification in (A) and (B) was relatively similar for the SINE region, indicating that BPL is less active on smaller DNA sequences. Even for these small sequences, however, there was a notable reduction in the amplification signal for all of the analyzed samples. Comparison of the PCR signal intensities between sample collection point (B) and (C) reflects the reduction of residual DNA due to intermediate purification steps.

Extrapolating from the gene-based analysis, and based directly on the SINE-based analysis, a total DNA level of <1 ng per dose, and often <100 pg per dose, is expected in a final vaccine.

Temperature

BPL treatment during virus inactivation had two independent steps: (1) add BPL to the virion-containing mixture at 2-8° C.; then (2) raise the temperature to 37° C. to hydrolyse BPL. The effects of the two BPL steps on MDCK DNA inactivation and fragmentation were investigated.

Figure 4:
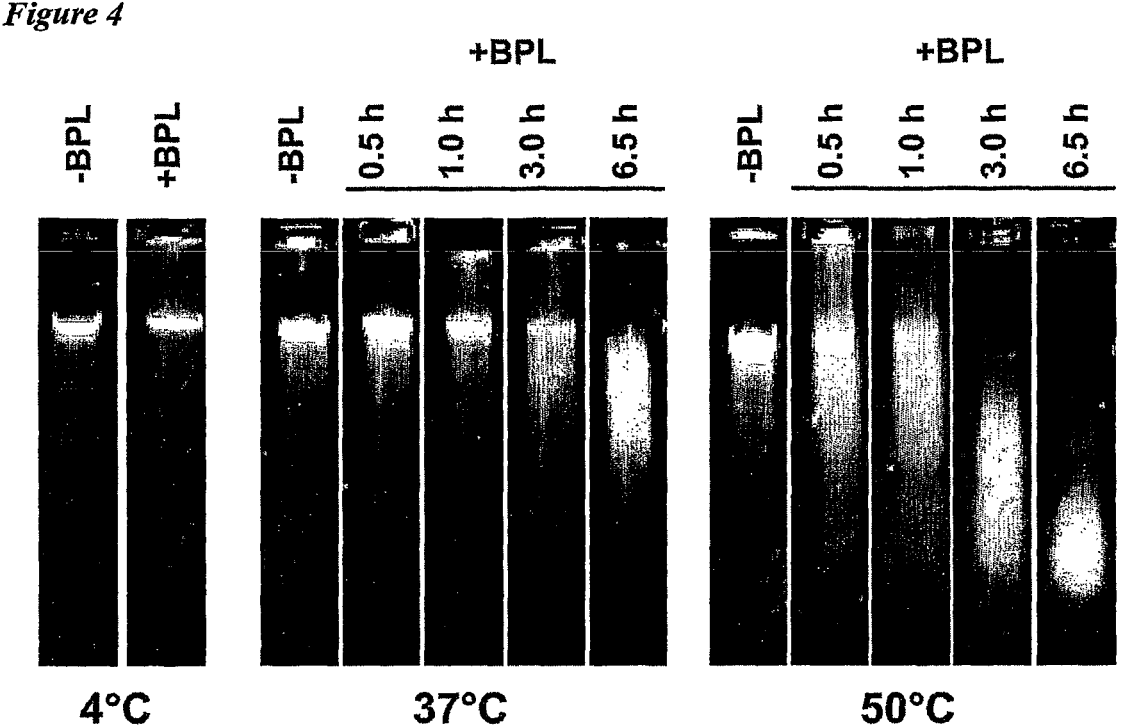

Purified genomic DNA from uninfected MDCK cells was treated with a final concentration of 0.05% (v/v) BPL at 2-8° C. for 16 hours, or at 37° C. or 50° C. for up to 6.5 hours. Fragmentation of DNA was checked afterwards, and results are shown in FIG. 4. These experiments reveal the activity of BPL against cellular DNA, but uninfected cells do not reflect the state of MDCK after viral growth because cellular DNA is already highly fragmented due to apoptosis.

Figure 5:
Figure 6:
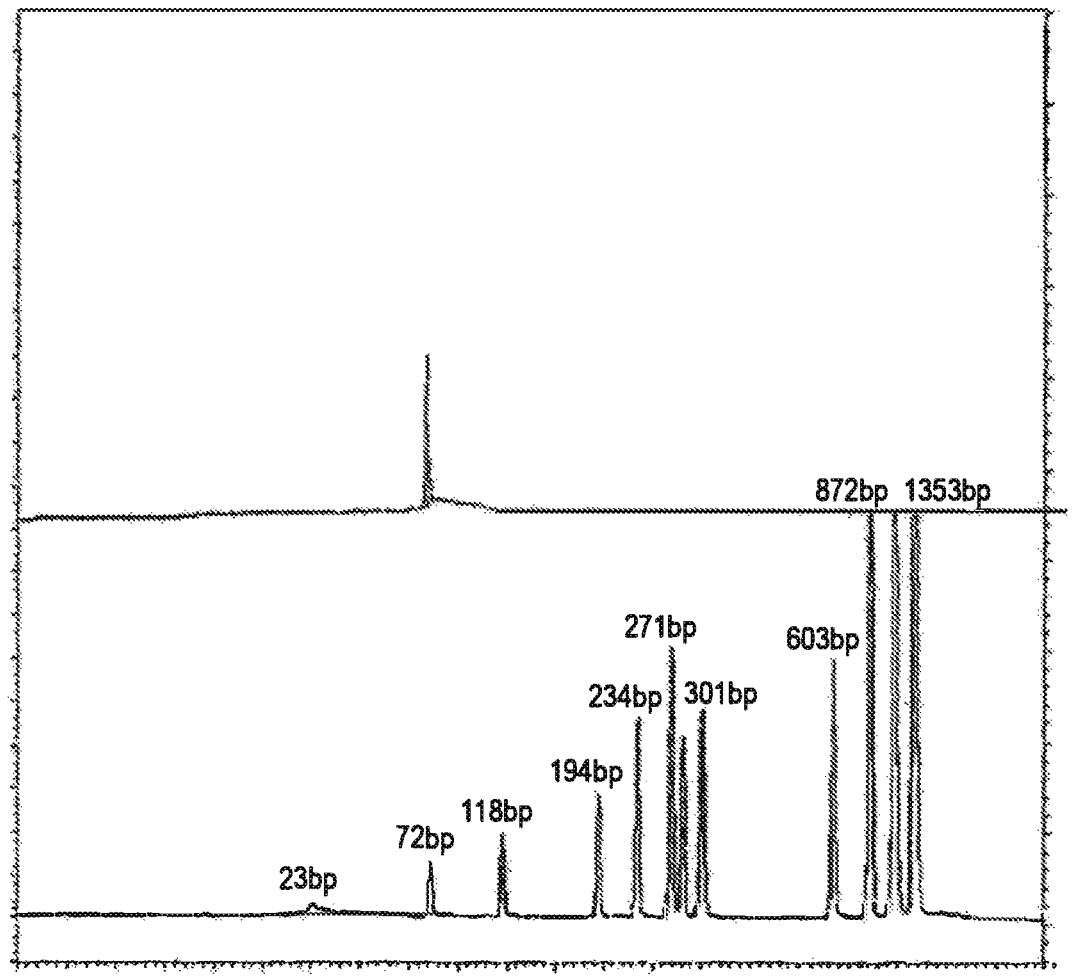

At 2-8° C., the difference between untreated and treated DNA on an agarose gel was negligible, suggesting that DNA fragmentation by BPL may not substantially occur during under these conditions. In contrast, DNA was greatly modified at both 37° C. and 50° C., with the higher temperature leading to an accelerated reaction kinetic. DNA from untreated cells showed a relatively distinct band in an agarose gel, with a light smear of degradation products (FIG. 5, lane 3). After a short BPL incubation at 37° C., however, MDCK DNA smeared down from the gel slots and band signal intensity decreased (FIG. 5, lane 2). Longer incubation periods resulted in the disappearance of large genomic DNA molecules and enhanced fragmentation of MDCK DNA.

In further experiments, BPL was first incubated with cells at 4° C. for 16 hours. In a first population, the temperature was raized to 37° C. for 2 hours; in a second population, BPL was removed by centrifugal filters and then the temperature was raized. Much lower (>2 log lower) residual DNA levels were seen in the first population.

Thus the DNA fragmentation observed during BPL treatment seems to occur mainly during the BPL hydrolysis step at 37° C. rather than during the virus inactivation step at 2-8° C.

It will be understood that the invention has been described by way of example only and modifications may be made whilst remaining within the scope and spirit of the invention.

The invention claimed is:

1. A vaccine comprising immunogenic proteins derived from two or more influenza virus strains propagated on cell culture, wherein the vaccine comprises 10 pg/mL to less than 20 ng/mL of residual cell culture DNA, wherein the length of the residual cell culture DNA is less than 200 base pairs, and wherein the cell culture is a mammalian cell culture or an avian cell culture.

2. The vaccine of claim 1, comprising less than 0.1% β-propiolactone (BPL).

3. The vaccine of claim 1, wherein the cell culture is selected from the group consisting of Madin Darby canine kidney (MDCK) cells, Vero cells, and human embryonic retinoblasts.

4. The vaccine of claim 1, further comprising an oil-in-water emulsion adjuvant.

5. The vaccine of claim 4, wherein the oil-in-water emulsion adjuvant comprises oil droplets having a sub-micron diameter.

6. The vaccine of claim 5, wherein the oil-in-water emulsion adjuvant comprises squalene.

7. The vaccine of claim 1, wherein the immunogenic proteins are viral antigens selected from the group consisting of hemagglutinin (HA), neuraminidase (NA), nucleoprotein (NP), matrix protein (M1), membrane protein (M2), and one or more of the transcriptase components (PB1, PB2 and PA).

8. The vaccine of claim 7, wherein the immunogenic proteins are NA.

9. The vaccine of claim 7, wherein the immunogenic proteins are HA.

10. The vaccine of claim 9, comprising about 7.5 μg, about 10 μg, or about 15 μg HA per influenza virus strain in a single dosage volume of about 0.5 mL.

11. The vaccine of claim 1, comprising immunogenic proteins derived from three or more influenza virus strains propagated on cell culture.

12. The vaccine of claim 1, wherein the length of the residual cell culture DNA is from 20 to 200 base pairs.

13. The vaccine of claim 1, wherein the length of the residual cell culture DNA is about 72 base pairs.

* * * * *